(12) United States Patent
Jeschke et al.

(10) Patent No.: US 8,084,452 B2
(45) Date of Patent: *Dec. 27, 2011

(54) SUBSTITUTED ENAMINOCARBONYL COMPOUNDS USED AS INSECTICIDES

(75) Inventors: Peter Jeschke, Bergisch Gladbach (DE); Robert Velten, Langenfeld (DE); Thomas Schenke, Bergisch Gladbach (DE); Otto Schallner, Monheim (DE); Michael Edmund Beck, Monheim (DE); Olga Malsam, Rösrath (DE); Ralf Nauen, Langenfeld (DE); Thomas Müller, Offenbach (DE); Christian Arnold, Langenfeld (DE); Erich Sanwald, Kiel (DE); Ulrich Görgens, Ratingen (DE)

(73) Assignee: Bayer Cropscience AG, Monheim (DE)

( * ) Notice: Subject to any disclaimer, the term of this patent is extended or adjusted under 35 U.S.C. 154(b) by 180 days.

This patent is subject to a terminal disclaimer.

(21) Appl. No.: 12/295,458

(22) PCT Filed: Mar. 19, 2007

(86) PCT No.: PCT/EP2007/002392
§ 371 (c)(1),
(2), (4) Date: Jan. 24, 2009

(87) PCT Pub. No.: WO2007/115646
PCT Pub. Date: Oct. 18, 2007

(65) Prior Publication Data
US 2010/0240705 A1    Sep. 23, 2010

(30) Foreign Application Priority Data

Mar. 31, 2006 (DE) .................. 10 2006 015 468

(51) Int. Cl.
| | |
|---|---|
| *A61K 31/506* | (2006.01) |
| *A61K 31/4427* | (2006.01) |
| *A61K 31/433* | (2006.01) |
| *A61K 31/4245* | (2006.01) |
| *A61K 31/425* | (2006.01) |
| *A61K 31/422* | (2006.01) |
| *A61K 31/4196* | (2006.01) |
| *A61K 31/4155* | (2006.01) |
| *C07D 271/06* | (2006.01) |
| *C07D 285/10* | (2006.01) |
| *C07D 275/02* | (2006.01) |
| *C07D 263/02* | (2006.01) |
| *C07D 261/02* | (2006.01) |
| *C07D 249/08* | (2006.01) |
| *C07D 241/02* | (2006.01) |
| *C07D 231/02* | (2006.01) |
| *C07D 203/02* | (2006.01) |

(52) U.S. Cl. ........ 514/247; 514/256; 514/336; 514/362; 514/365; 514/374; 514/383; 514/438; 546/329; 548/131; 548/134; 548/215; 548/255

(58) Field of Classification Search .................. 548/131, 548/134, 215, 255; 546/329; 514/247, 256, 514/336, 362, 365, 374, 383, 438
See application file for complete search history.

(56) References Cited

U.S. PATENT DOCUMENTS 7,417,150 B2    8/2008  Jeschke et al.

FOREIGN PATENT DOCUMENTS

| EP | 0 539 588 A1 * | 1/1992 |
|---|---|---|
| EP | 0 539 588 | 5/1993 |
| WO | WO 97/30032 | 8/1997 |
| WO | WO 98/33772 | 8/1998 |
| WO | 02085870 | 10/2002 |
| WO | WO 2006/037475 | 4/2006 |

OTHER PUBLICATIONS

U.S. Application No. 2009-295355, commonly assigned to Bayer CropScience.*
International Search Report, App. No. PCT/EP2007/002392, dated Jun. 25, 2007 (6 pages).

* cited by examiner

*Primary Examiner* — Joseph K. McKane
*Assistant Examiner* — Janet L Coppins
(74) *Attorney, Agent, or Firm* — Baker, Donelson, Bearman, Caldwell & Berkowitz, PC

(57) ABSTRACT

The present application relates to novel substituted enaminocarbonyl compounds, to processes for their preparation and to their use for controlling animal pests, especially arthropods, in particular insects.

17 Claims, No Drawings

SUBSTITUTED ENAMINOCARBONYL COMPOUNDS USED AS INSECTICIDES

CROSS REFERENCE TO RELATED APPLICATIONS

This application is a §371 National Stage Application of PCT/EP2007/002392 filed Mar. 19, 2007 which claims priority from German Application 10 2006 015 468.1 filed Mar. 31, 2006.

BACKGROUND OF THE INVENTION

1. Field of the Invention

The present application relates to novel substituted enaminocarbonyl compounds, to processes for their preparation and to their use for controlling animal pests, especially arthropods, in particular insects.

2. Description of Related Art

Substituted enaminocarbonyl compounds are already known as insecticidally active compounds (cf. EP 0 539 588 A1, DE 102004047922 A1).

SUMMARY OF THE INVENTION

This invention now provides novel compounds of the formula (I)

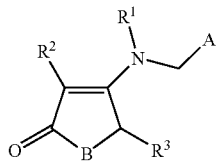
(I)

in which
A represents one of the radicals pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which are optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or
A represents a radical

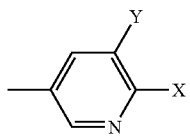

in which
X represents halogen, alkyl or haloalkyl,
Y represents halogen, alkyl, haloalkyl, haloalkoxy, azido or cyano,
B represents oxygen, sulphur or methylene,
$R^1$ represents haloalkyl, haloalkenyl, halocycloalkyl or halocycloalkylalkyl,
$R^2$ represents hydrogen or halogen and
$R^3$ represents hydrogen or alkyl.

Furthermore, it has been found that the novel compounds of the formula (I) are obtained when
a) compounds of the formula (II)

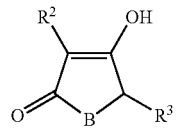
(II)

in which
B, $R^2$ and $R^3$ are as defined above
are reacted with compounds of the formula (III)

$$HN(R^1)\text{—}CH_2\text{-}A \quad (III)$$

in which
A and $R^1$ are as defined above,
if appropriate in the presence of a suitable diluent and if appropriate in the presence of an acidic auxiliary (process 1), or when
b) compounds of the formula (I)

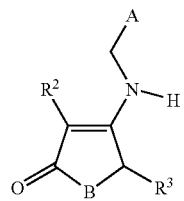
(Ia)

in which
A, B, $R^2$ and $R^3$ are as defined above
are reacted with compounds of the formula (IV)

$$E\text{-}R^1 \quad (IV)$$

in which
E represents a suitable leaving group such as, for example, halogen (in particular bromine, chlorine, iodine) or O-sulphonylalkyl and O-sulphonylaryl (in particular O-mesyl, O-tosyl),
if appropriate in the presence of a suitable diluent and if appropriate in the presence of an acid acceptor (process 2), or when
c) compounds of the formula (II)

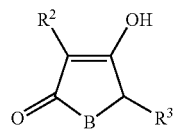
(II)

in which
B, $R^2$ and $R^3$ are as defined above,
are, in a first reaction step, reacted with compounds of the formula (V)

$$H_2N\text{—}R^1 \quad (V)$$

in which
$R^1$ is as defined above,
if appropriate in the presence of a suitable diluent and if appropriate in the presence of an acidic auxiliary, and the resulting compounds of the formula (VI)

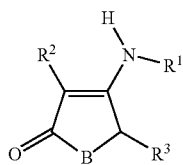

(VI)

in which
B, R$^1$, R$^2$ and R$^3$ are as defined above
are then, in a second reaction step, reacted with compounds of the formula (VII)

E-CH$_2$-A (VII)

in which
E and A are as defined above,
if appropriate in the presence of a suitable diluent and if appropriate in the presence of an acid acceptor (process 3).

Finally, it has been found that the novel compounds of the formula (I) have strongly pronounced biological properties and are suitable especially for controlling animal pests, in particular insects, arachnids and nematodes encountered in agriculture, in forests, in the protection of stored products and in the protection of materials, and also in the hygiene sector.

Depending, where appropriate, on the nature of the substituents, the compounds of the formula (I) may be present as geometrical and/or as optically active isomers or corresponding isomer mixtures of varying composition. The invention relates both to the pure isomers and the isomer mixtures.

DETAILED DESCRIPTION OF A PREFERRED EMBODIMENT

The formula (I) provides a general definition of the compounds according to the invention.

Preferred substituents or ranges of the radicals given in the formulae mentioned above and below are illustrated below.

A preferably represents pyrimidin-5-yl which is optionally substituted in the 2-position by halogen or C$_1$-C$_4$-alkyl, represents 1H-pyrazol-4-yl which is optionally substituted in the 1-position by C$_1$-C$_4$-alkyl and in the 3-position by halogen, represents 1H-pyrazol-5-yl which is optionally substituted in the 2-position by halogen or C$_1$-C$_4$-alkyl, represents isoxazol-5-yl which is optionally substituted in the 3-position by halogen or C$_1$-C$_4$-alkyl, represents 1,2,4-oxadiazol-5-yl which is optionally substituted in the 3-position by halogen or C$_1$-C$_4$ alkyl, represents 1-methyl-1,2,4-triazol-3-yl, or represents 1,2,5-thiadiazol-3-yl, furthermore A preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-iodo-6-bromopyrid-3-yl, 5-fluoro-6-iodopyrid-3-yl, 5-chloro-6-iodopyrid-3-yl, 5-bromo-6-iodopyrid-3-yl, 5,6-diiodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

B preferably represents oxygen or methylene.

R$^1$ preferably represents in each case fluorine-substituted C$_1$-C$_5$-alkyl, C$_2$-C$_5$-alkenyl, C$_3$-C$_5$-cycloalkyl or C$_3$-C$_5$-cycloalkylalkyl.

R$^2$ preferably represents hydrogen or halogen.

R$^3$ preferably represents hydrogen or C$_1$-C$_3$-alkyl.

A particularly preferably represents one of the radicals 2-methylpyrimidin-5-yl, 2-chloropyrimid-5-yl, 1H-pyrazol-4-yl which is optionally substituted in the 1-position by methyl, ethyl, and in the 3-position by chlorine, 1H-pyrazol-5-yl, 2-methylpyrazol-5-yl, 2-bromothiazolyl, isoxazol-5-yl which is optionally substituted in the 3-position by methyl, ethyl, chlorine or bromine, 3-methyl-1,2,4-oxadiazol-5-yl, 1-methyl-1,2,4-triazol-3-yl or 1,2,5-thiadiazol-3-yl, furthermore A particularly preferably represents one of the radicals 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl or 5-methyl-6-bromopyrid-3-yl.

B particularly preferably represents oxygen or methylene.

R$^1$ particularly preferably represents 2-fluoroethyl, 2,2-difluoroethyl or 2-fluorocyclopropyl.

R$^2$ particularly preferably represents hydrogen, fluorine, chlorine or bromine.

R$^3$ particularly preferably represents hydrogen or methyl.

A very particularly preferably represents one of the radicals 2-methylpyrimidin-5-yl, 2-chloropyrimid-5-yl, 3-methylisoxazol-5-yl, 3-bromoisoxazol-5-yl, 5-fluoro-6-chloropyrid-3-yl, 5,6-dichloropyrid-3-yl or 5-fluoro-6-bromopyrid-3-yl.

B very particularly preferably represents oxygen.

R$^1$ very particularly preferably represents 2,2-difluoroethyl.

R$^2$ particularly preferably represents hydrogen.

R$^3$ particularly preferably represents hydrogen.

In a special group of compounds of the formula (I), A represents 2-methylpyrimidin-5-yl,

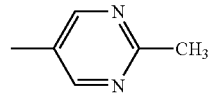

In a further special group of compounds of the formula (I), A represents 2-chloropyrimidin-5-yl,

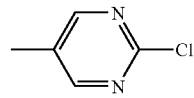

In a further special group of compounds of the formula (I), A represents 3-methylisoxazol-5-yl,

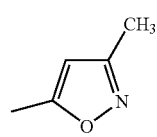

In a further special group of compounds of the formula (I),
A represents 3-bromoisoxazol-5-yl,

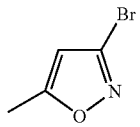

In a further special group of compounds of the formula (I),
A represents 5-fluoro-6-chloropyrid-3-yl,

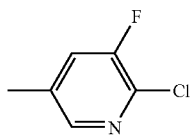

In a further special group of compounds of the formula (I),
A represents 5,6-dichloropyrid-3-yl

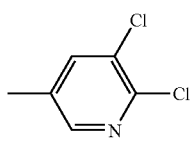

In a further special group of compounds of the formula (I),
A represents 5-fluoro-6-bromopyrid-3-yl

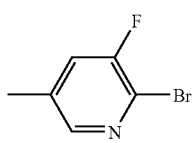

In a further special group of compounds of the formula (I),
A represents 5-fluoro-6-iodopyrid-3-yl

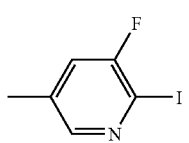

In a further special group of compounds of the formula (I),
A represents 5-chloro-6-iodopyrid-3-yl

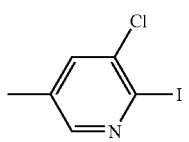

Hereinbelow, a further group of preferred compounds of the formula (I) is defined in which A represents a pyrimidin-5-yl radical which is substituted in the 2-position by halogen or halo-$C_1$-$C_4$-alkyl,
or
A represents a radical

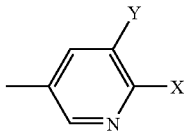

in which
X represents halogen, $C_1$-$C_1$-alkyl, halo-$C_1$-$C_4$-alkyl,
Y represents halogen, halo-$C_1$-$C_4$-alkyl, halo-$C_1$-$C_4$-alkoxy, azido or cyano,
B represents oxygen, sulphur or methylene,
$R^1$ represents halo-$C_1$-$C_3$-alkyl, halo-$C_2$-$C_3$-alkenyl, halocyclopropyl (where halogen represents in particular fluorine or chlorine),
$R^2$ represents hydrogen or halogen and
$R^3$ represents hydrogen or methyl.
A preferably represents 2-chloropyrimidin-5-yl or 2-trifluoromethylpyrimidin-5-yl,
furthermore
A preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.
B preferably represents oxygen or methylene.
$R^1$ preferably represents in each case fluorine-substituted $C_1$-$C_3$-alkyl, $C_2$-$C_3$-alkenyl or cyclopropyl.
$R^2$ preferably represents hydrogen or halogen (where halogen represents in particular fluorine or chlorine).
$R^3$ preferably represents hydrogen.
A particularly preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.
B particularly preferably represents oxygen.
$R^1$ particularly preferably represents 2-fluoroethyl, 2,2-difluoroethyl or 2-fluorocyclopropyl.
$R^2$ particularly preferably represents hydrogen.
$R^3$ particularly preferably represents hydrogen.
A very particularly preferably represents 5-fluoro-6-chloropyrid-3-yl or 5-fluoro-6-bromopyrid-3-yl.
B very particularly preferably represents oxygen.
$R^1$ very particularly preferably represents 2,2-difluoroethyl.
$R^2$ particularly preferably represents hydrogen.
$R^3$ particularly preferably represents hydrogen.
In a special group of compounds of the formula (I), $R^3$ represents hydrogen, B represents oxygen and A represents 2-chloropyrimidin-5-yl,

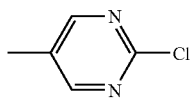

In a further special group of compounds of the formula (I), $R^3$ represents hydrogen, B represents oxygen and A represents 5-fluoro-6-chloropyrid-3-yl,

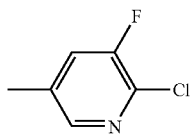

In a further special group of compounds of the formula (I), $R^3$ represents hydrogen, B represents oxygen and A represents 5,6-dichloropyrid-3-yl

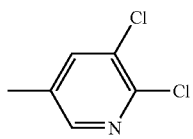

In a further special group of compounds of the formula (I), $R^3$ represents hydrogen, B represents oxygen and A represents 5-bromo-6-chloropyrid-3-yl

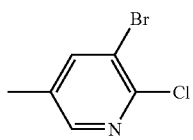

In a further special group of compounds of the formula (I), $R^3$ represents hydrogen, B represents oxygen and A represents 5-methyl-6-chloropyrid-3-yl

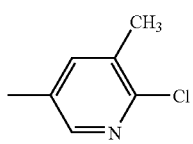

In a further special group of compounds of the formula (I), $R^3$ represents hydrogen, B represents oxygen and A represents 5-fluoro-6-bromopyrid-3-yl

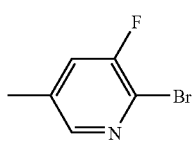

In a further special group of compounds of the formula (I), $R^3$ represents hydrogen, B represents oxygen and A represents 5-chloro-6-bromopyrid-3-yl

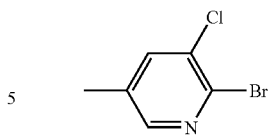

In a further special group of compounds of the formula (I), $R^3$ represents hydrogen, B represents oxygen and A represents 5-chloro-6-iodopyrid-3-yl

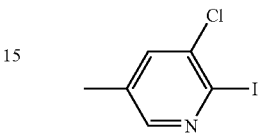

In a special group of compounds of the formula (I), $R^2$ and $R^3$ represent hydrogen, B represents oxygen and A represents 2-chloropyrimidin-5-yl,

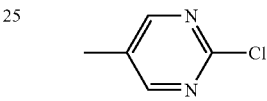

In a further special group of compounds of the formula (I), $R^2$ and $R^3$ represent hydrogen, B represents oxygen and A represents 5-fluoro-6-chloropyrid-3-yl,

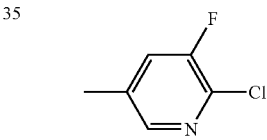

In a further special group of compounds of the formula (I), $R^2$ and $R^3$ represent hydrogen, B represents oxygen and A represents 5,6-dichloropyrid-3-yl

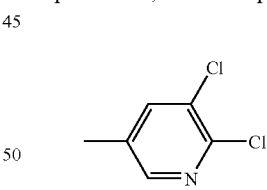

In a further special group of compounds of the formula (I), $R^2$ and $R^3$ represent hydrogen, B represents oxygen and A represents 5-bromo-6-chloropyrid-3-yl

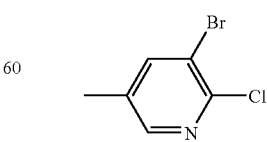

In a further special group of compounds of the formula (I), $R^2$ and $R^3$ represent hydrogen, B represents oxygen and A represents 5-methyl-6-chloropyrid-3-yl

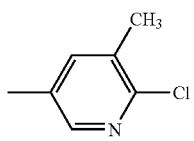

In a further special group of compounds of the formula (I), $R^2$ and $R^3$ represent hydrogen, B represents oxygen and A represents 5-fluoro-6-bromopyrid-3-yl

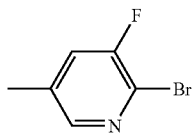

In a further special group of compounds of the formula (I), $R^2$ and $R^3$ represent hydrogen, B represents oxygen and A represents 5-chloro-6-bromopyrid-3-yl

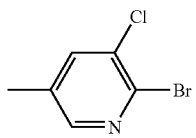

In a further special group of compounds of the formula (I), $R^2$ and $R^3$ represent hydrogen, B represents oxygen and A represents 5-chloro-6-iodopyrid-3-yl

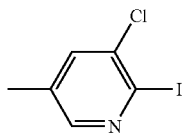

In a further special group of compounds of the formula (I), $R^2$ and $R^3$ represent hydrogen, B represents methylene and A represents 2-chloropyrimidin-5-yl,

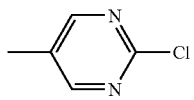

In a further special group of compounds of the formula (I), $R^2$ and $R^3$ represent hydrogen, B represents methylene and A represents 5-fluoro-6-chloropyrid-3-yl,

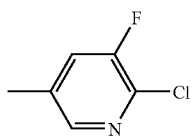

In a further special group of compounds of the formula (I), $R^2$ and $R^3$ represent hydrogen, B represents methylene and A represents 5,6-dichloropyrid-3-yl

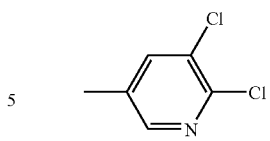

In a further special group of compounds of the formula (I), $R^2$ and $R^3$ represent hydrogen, B represents methylene and A represents 5-bromo-6-chloropyrid-3-yl

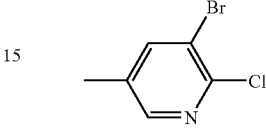

In a further special group of compounds of the formula (I), $R^2$ and $R^3$ represent hydrogen, B represents methylene and A represents 5-methyl-6-chloropyrid-3-yl

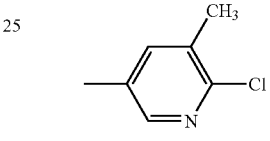

In a further special group of compounds of the formula (I), $R^2$ and $R^3$ represent hydrogen, B represents methylene and A represents 5-fluoro-6-bromopyrid-3-yl

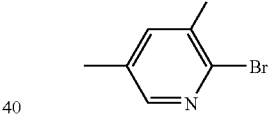

In a further special group of compounds of the formula (I), $R^2$ and $R^3$ represent hydrogen, B represents methylene and A represents 5-chloro-6-bromopyrid-3-yl

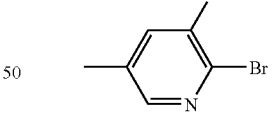

In a further special group of compounds of the formula (I), $R^2$ and $R^3$ represent hydrogen, B represents methylene and A represents 5-chloro-6-iodo-pyrid-3-yl

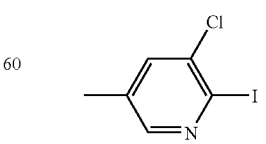

In a further special group of compounds of the formula (I), $R^1$ represents difluoromethyl, $R^2$ and $R^3$ represent hydrogen and B represents oxygen.

In a further special group of compounds of the formula (I), $R^1$ represents 2-fluoroethyl, $R^2$ and $R^3$ represent hydrogen and B represents oxygen.

In a further special group of compounds of the formula (I), $R^1$ represents 2,2-difluoroethyl, $R^2$ an $R^3$ represent hydrogen and B represents oxygen In a further special group of compounds of the formula (I), $R^1$ represents difluoromethyl, $R^2$ and $R^3$ represent hydrogen and B represents methylene.

In a further special group of compounds of the formula (I), $R^1$ represents 2-fluoroethyl, $R^2$ and $R^3$ represent hydrogen and B represents methylene.

In a further special group of compounds of the formula (I), $R^1$ represents 2,2-difluoroethyl, $R^2$ and $R^3$ represent hydrogen and B represents methylene.

The general or preferred radical definitions or illustrations given above apply both to the end products and, correspondingly, to precursors and intermediates. These radical definitions can be combined with one another as desired, i.e. including combinations between the respective preferred ranges.

Preference according to the invention is given to compounds of the formula (I) which contain a combination of the meanings listed above as being preferred (preferable).

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

If, in the process 1 according to the invention for preparing the novel compounds of the formula (I), the compound of the formula (II) is, for example, tetronic acid and the compound of the formula (III) is, for example, N-[(6-chloro-5-fluoropyridin-3-yl)methyl]-2,2-difluoroethane-1-amine, preparation process 1 can be represented by the reaction scheme I below:

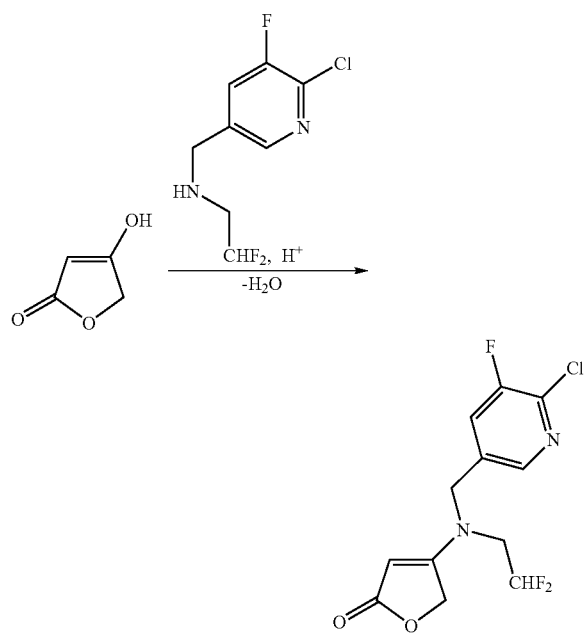

The formula (II) provides a general definition of the compounds required as starting materials for carrying out the process 1 according to the invention.

In this formula (II), B, $R^2$ and $R^3$ preferably represent those radicals which have already been mentioned in connection with the description of the compounds of the formula (I) according to the invention as preferred substituents.

Some of the compounds of the formula (II) can be obtained commercially or by methods known form the literature (cf., for example, compounds of the general formula (II) in which B represents oxygen:tetronic acids (Said, A. Speciality Chemicals Magazine (1984), 4(4), 7-8; Rao, Y. S. Chem. Rev. (1976), 76, 625-694; Tejedor, D.; Garcia-Tellado, F. Org. Preparations and Procedures International (2004), 36, 35-59; Reviews); compounds of the general formula (II) in which B represents sulphur:thiotetronic acids (Thomas, E. J. Special Publication—Royal Society of Chemistry (1988), 65 (Top. Med. Chem.), 284-307, Review), compounds of the general formula (II) in which B represents methylene:cyclopentane-1,3-dione (Schick, Hans; Eichhorn, Inge. Synthesis (1989), (7), 477-492, Review).

The formula (III) provides a general definition of the compounds furthermore to be used as starting materials for carrying out the process 1 according to the invention.

In formula (III), A and $R^1$ have the meanings already mentioned in connection with the description of the compounds of the formula (I) according to the invention.

Some of the compounds of the formula (III) can be obtained commercially or by methods known from the literature (cf., for example, S. Patai "The Chemistry of Amino Group", Interscience Publishers, New York, 1968; compounds of the general formula (III) in which $R^1$ represents hydrogen:primary amines, compounds of the general formula (III) in which $R^1$ represents haloalkyl, haloalkenyl or halocycloalkyl: secondary amines).

Some of the compounds of the formula (VII) are commercially available, some are known, or they can be obtained by known methods.

Routes for preparing compounds of the formula (VII) are illustrated in reaction scheme III.

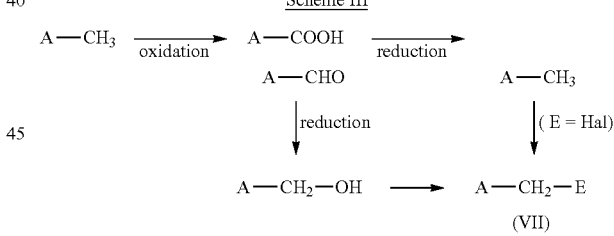

E = Hal, for example chlorine, bromine, iodine; O-tosyl, O-mesyl,

A = as defined above, for example 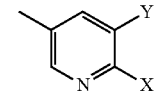

Methyl-substituted compounds (A-CH$_3$), for example, can be converted by oxidation into corresponding carboxylic acids (A-COOH, for example 5-fluoro-6-bromonicotinic acid: F. L. Setliff, G. O. Rankin, J. Chem. Eng. Data (1972), 17, 515-516; 5-chloro-6-bromonicotinic acid and 5,6-dibromonicotinic acid: F. L. Setliff et al., J. Chem. Eng. Data (1981), 26, 332-333; 5-iodo-6-bromonicotinic acid: F. L. Setliff et al., J. Chem. Eng. Data (1978), 23, 96-97, 5-fluoro-6-iodonicotinic acid and 5-bromo-6-iodonicotinic acid: F. L. Setliff et al., J. Chem. Eng. Data (1973), 18, 449-450, 5-chloro-6-iodonicotinic acid: F. L. Setliff, J. E. Lane J. Chem. Eng. Data (1976), 21, 246-247) or carboxylic esters (for example methyl 5-methyl-6-fluoronicotinate: WO 9833772 A1, 1998; methyl 5-methyl-6-bromonicotinate: WO 9730032 A1, 1997).

The carboxylic acids (A-COOH) can then be converted by methods known from the literature into the corresponding hydroxymethyl compounds (A-CH$_2$—OH), which are then reacted by methods known from the literature to give activated hydroxymethyl compounds (A-CH$_2$-E, E=O-tosyl, O-mesyl) or halomethyl compounds (A-CH$_2$-E, E=Hal). The latter can also be obtained from corresponding compounds which contain a methyl group (A-CH$_3$) using suitable halogenating agents known from the literature. The syntheses of the following compounds: 5-chloromethyl-2-methylpyrimidine (U. Eiermann et al., Chem. Ber. (1990), 123, 1885-9); 3-chloromethyl-5-bromo-6-chloropyridine, 3-bromo-5-iodo-6-chloropyridine (S. Kagabu et al., J. Pestic. Sci. (2005), 30, 409-413) may be mentioned as examples for this procedure.

Compounds of the formula (VII) in which A represents a 5,6-disubstituted pyrid-3-yl radical can also be obtained by methods known from the literature. Suitable starting materials known from the literature are, for example, the 6-halo-substituted 5-nitro-β-picolines (A-1), which can be modified by known literature procedures, as shown in reaction scheme IV.

acid, 5-bromo-6-chloronicotinic acid and 5-bromo-6-bromonicotinic acid: F. L. Setliff J. Chem. Engineering Data (1970), 15, 590-591; 5-chloro-6-bromonicotinic acid and 5-iodo-6-bromonicotinic acid: Setliff, F. L., Greene, J. S. J. Chem. Engineering Data (1978), 23, 96-97; also known is 5-chloro-6-trifluoromethylnicotinic acid: F. Cottet et al., Synthesis (2004), 10, 1619-1624), which can be converted in the presence of reducing agents into the corresponding hydroxymethylated pyridines (A-5) (for example 5-bromo-6-chloro-3-hydroxymethylpyridine: Kagabu, S. et al., J. Pestic. Sci. (2005), 30, 409-413).

By reduction of 6-chloro-5-nitronicotinic acid (A-4, X=Cl, Y=NO$_2$; Boyer, J. H.; Schoen, W., J. Am. Chem. Soc. (1956), 78, 423-425), it is possible to form 6-chloro-3-hydroxymethyl-5-nitro-pyridine (A-5, X=Cl, Y=NO$_2$; Kagabu, S. et al., J. Med. Chem. (2000), 43, 5003-5009), which is then reduced to 6-chloro-3-hydroxymethyl-5-aminopyridine (A-5, X=Cl, Y=NH$_2$; Kagabu, S. et al., J. Med. Chem. (2000), 43, 5003-5009) and, via diazotisation and reaction with hydroxylamine, converted into 6-chloro-3-hydroxymethyl-5-azidopyridine (A-5, X=Cl, Y=N$_3$; Kagabu, S. et al., J. Med. Chem. (2000), 43, 5003-5009). Subsequent halogenation with thionyl chloride gives 6-chloro-3-chloromethyl-5-azidopyridine (VII, X=Cl, Y=N$_3$, E=Cl; Kagabu, S. et al., J. Med. Chem. (2000), 43, 5003-5009).

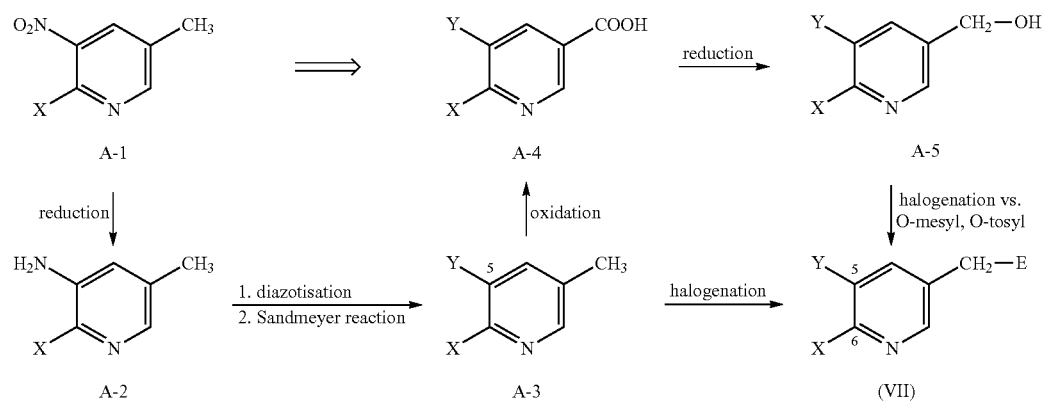

Scheme IV

X, Y = halogen, for example fluorine, chlorine, bromine, iodine
E = halogen, O-mesyl, O-tosyl The reduction of the nitro group in 6-halo-substituted 5-nitro-β-picolines (A-1), for example, gives 6-halo-substituted 5-amino-β-picolines (A-2, for example 5-amino-6-chloro-β-picoline and 5-amino-6-bromo-β-picoline: Setliff, F. L. Org. Preparations and Preparations Int. (1971), 3, 217-222; Kagabu, S. et al. J. Pestic. Sci. (2005), 30, 409-413). Subsequent diazotisation and Sandmeyer reaction (C. F. H. Allen, J. R. Thirtle, Org. Synth., Coll. Vol. III, 1955, p. 136) allows the introduction of halogen substituents in the 5-position (A-3, for example 5-fluoro-6-chloro-β-picoline and 5-fluoro-6-bromo-β-picoline: Setliff, F. L. Org. Preparations and Preparations Int. (1971), 3, 217-222; 5-iodo-6-chloro-β-picoline: Kagabu, S. et al. J. Pestic. Sci. (2005), 30, 409-413; 5,6-dichloropicoline: Setliff, F. L.; Lane, J. E. J. Chem. Engineering Data (1976), 21, 246-247). The oxidation of the methyl group in the 5,6-disubstituted β-picolines (A-3) leads to the corresponding 5,6-disubstituted nicotinic acids (A-4, for example 5-fluoro-6-chloronicotinic acid and 5-fluoro-6-bromonicotinic acid: Setliff F. L., Rankin G. O. J. Chem. Engineering Data (1972), 17, 515-516; 5-bromo-6-fluoronicotinic Alternatively, halogenation of the methyl group in the 3-position of (A-3) gives compounds of the formula (VII) in which E represents halogen (for example: 3-bromomethyl-6-chloro-5-fluoropyridine, 3-bromomethyl-6-chloro-5-iodopyridine: Kagabu, S. et al. J. Pestic. Sci. (2005), 30, 409-413). When 6-halo-substituted 5-nitro-β-picolines (A-3; Y=NO$_2$) are used, there may be initial halogenation of the methyl group in the 3-position (for example 3-bromomethyl-6-chloro-5-nitro-pyridine: Kagabu, S. et al., J. Pestic. Sci. (2005), 30, 409-413). If appropriate, the nitro group may also be reduced at a later stage in the reaction sequence.

Also known from the literature is the introduction of substituents in the 5-position (for example Y=N$_3$) of compounds of the formula (VII) in which E represents N-morpholino. This radical can subsequently very easily be replaced by halogen (E=Hal) (cf. S. Kagabu et al., J. Med. Chem. 2000, 43, 5003-5009; reaction conditions: ethyl chloroformate, tetrahydrofuran, 60° C.).

In general, it is possible to replace halogen atoms in the vicinity of the pyridine nitrogen by other halogen atoms or halogenated groups such as, for example, trifluoromethyl (transhalogenation, for example: chlorine for bromine or iodine; bromine for iodine or fluorine; iodine for fluorine or trifluoromethyl). Thus, a further alternative synthesis route entails exchange of the halogen atom (for example X=Cl) in the 6-position of the pyrid-5-yl radical (for example in A-4 where X, Y=Cl; 5,6-dichloronicotinic acid: Setliff, F. L.; Lane, J. E. J. Chem. Engineering Data (1976), 21, 246-247) for another halogen atom, for example iodine or fluorine (for example: A-4 where X=I; 5-bromo-6-iodonicotinic acid and A-4 where X=F; 5-bromo-6-fluoronicotinic acid: Setliff, F. L.; Price, D. W. J. Chem. Engineering Data (1973), 18, 449-450). However, this transhalogenation may also, if appropriate, be carried out later in suitable compounds of the formula (I), as illustrated in reaction scheme X and by the working examples further below.

For preparing compounds of the formula (III), for example, compounds of the formula (VII) in which A and E have the meanings mentioned further above are reacted with compounds of the formula (V) in which $R^1$ has the meanings mentioned further above, if appropriate in the presence of diluents and if appropriate in the presence of the basic reaction auxiliaries mentioned in the description of preparation process 2 (cf. N-alkylation, Scheme V).

Scheme V

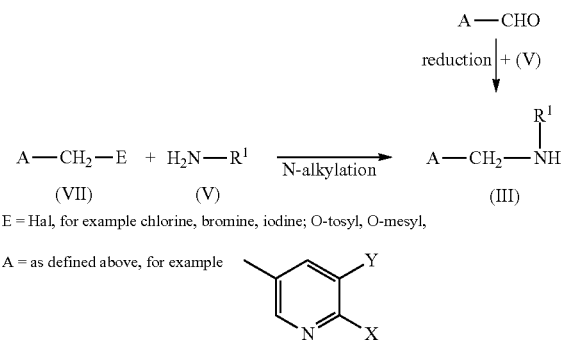

E = Hal, for example chlorine, bromine, iodine; O-tosyl, O-mesyl,

A = as defined above, for example

In certain cases, it is alternatively also possible to prepare compounds of the formula (III) from the corresponding aldehydes (A-CHO) and compounds of the formula (V) by reductive amination (cf. Houben-Weyl, Methoden der Organischen Chemie [Methods of Organic Chemistry], vol. XI/1, Georg Thieme Verlag Stuttgart, p. 602).

In general, it is advantageous to carry out the preparation process 1 according to the invention in the presence of diluents. Diluents are advantageously employed in such an amount that the reaction mixture remains readily stirrable during the entire process. Suitable diluents for carrying out the process 1 according to the invention are all inert organic solvents.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dipropylether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methylmorpholine, pyridine and tetramethylenediamine; nitrated hydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and also compounds, such as tetrahydrothiophene dioxide and dimethyl sulphoxide, tetramethylene sulphoxide, dipropyl sulphoxide, benzylmethyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example white spirits with components having boiling points in the range of, for example, from 40° C. to 250° C., cymene, petroleum fractions having a boiling point interval of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

It is also possible to use mixtures of the solvents and diluents mentioned for the process according to the invention.

However, preferred diluents for carrying out the process according to the invention are aromatic hydrocarbons, such as benzene, toluene, chlorobenzene, bromobenzene, nitrobenzene or xylene, in particular benzene and toluene.

The preparation of compounds of the formula (I) according to preparation process 1 is generally carried out by reacting compounds of the formula (II) with compounds of the formula (III) in the presence of an acidic auxiliary in a diluent.

The reaction time is generally from 10 minutes to 48 hours.

The reaction is carried out at temperatures between −10° C. and +200° C., preferably between +10° C. and 180° C., particularly preferably between 20° C. and 140° C. The reaction is preferably carried out under reaction conditions which allow water to be separated off or to be removed, for example with the aid of a water separator or by adding suitable molecular sieves, which also allow water to be removed.

In principle, the reaction can be carried out under atmospheric pressure. The reaction is preferably carried out under atmospheric pressure or under pressures of up to 15 bar and, if appropriate, under an atmosphere of protective gas (nitrogen, helium or argon).

For carrying out the process 1 according to the invention, in general from 0.5 to 4.0 mol, preferably from 0.7 to 3.0 mol, particularly preferably from 1.0 to 2.0 mol of amino compound of the formula (III) are employed per mole of the compound of the formula (II).

Furthermore, for carrying out the process 1 according to the invention, in general catalytic amounts of an acidic auxiliary are added.

Suitable acidic auxiliaries are, for example, p-toluenesulphonic acid or acetic acid.

After the reaction has gone to completion, the entire reaction mixture is concentrated. The products obtained after work-up can be purified in a customary manner by recrystallisation, distillation under reduced pressure or column chromatography (cf. also the Preparation Examples).

If, in the process 2 according to the invention for preparing the novel compounds of the formula (I), the compound of the formula (Ia) is, for example, 4-[[(6-bromo-5-chloropyridin-3-yl)methyl]amino]furan-2(5H)-one and the compound of the formula (IV) is 1-bromo-1,1-dichloroprop-1-ene, preparation process 2 can be represented by reaction scheme VI below:

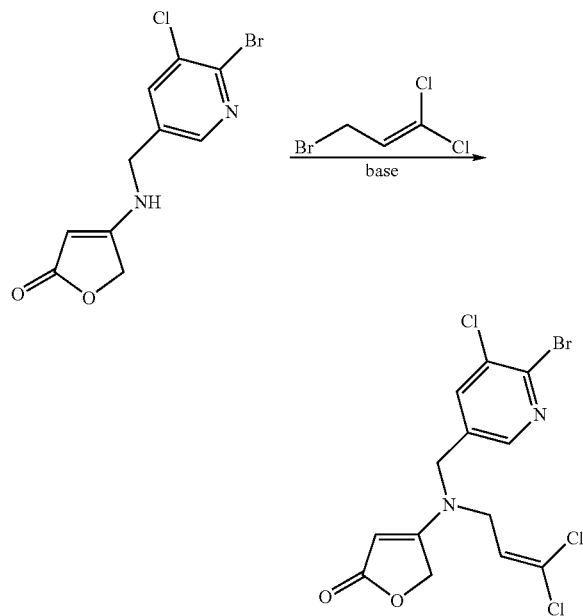

The formula (Ia) provides a general definition of the compounds required as starting materials for carrying out the process 2 according to the invention.

In this formula (Ia), A, B, $R^2$ and $R^3$ preferably represent those radicals which have already been mentioned in connection with the description of the compounds of the general formula (I) according to the invention as preferred substituents.

The compounds of the formula (Ia) can be obtained by preparation process 1, described further above, for example by reacting compounds of the formula (II) with compounds of the formula (III) in which $R^1$ represents hydrogen.

The formula (IV) provides a general definition of the compounds further to be used as starting materials for carrying out the process 2 according to the invention.

In formula (IV), E and $R^1$ have the meanings already mentioned in connection with the description of the compounds of the formula (I) according to the invention.

Some of the compounds of the formula (IV) are commercially available, or they can be obtained by methods known from the literature (cf., for example, 1-bromo-1,1-dichloropropene: WO 8800183 A1 (1988); compounds of the formula (IV) in which E represents halogen, such as chlorine, bromine and iodine: Houben-Weyl, Methoden der Organischen Chemie, vol. V/3, Georg Thieme Verlag Stuttgart, p. 503 and vol. V/4 p. 13, 517; compounds of the formula (IV) in which E represents mesylate: Crossland, R. K., Servis, K. L. J. Org. Chem. (1970), 35, 3195; compounds of the formula (IV) in which E represents tosylate: Roos, A. T. et al., Org. Synth., Coll. Vol. I, (1941), 145; Marvel, C. S., Sekera, V. C. Org. Synth., Coll. Vol. III, (1955), 366.

In general, it is advantageous to carry out the preparation process 2 according to the invention in the presence of a diluent and, if appropriate, in the presence of a basic reaction auxiliary.

Diluents are advantageously employed in such an amount that the reaction mixture remains readily stirrable during the entire process. Suitable diluents for carrying out the process 2 according to the invention are all inert organic solvents.

Preferred diluents for carrying out the process 2 according to the invention are ethers, such as methyl tert-butyl ether, n-butyl ether, anisole, phenetole, cyclohexyl methyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxid; amides, such as hexamethylenephosphoric triamide, formamide, N-methylformamide, N,N-dimethylformamide, N,N-dipropylformamide, N,N-dibutylformamide; aromatic hydrocarbons, such as N-methylbenzene, toluene, chlorobenzene, bromobenzene, nitrobenzene, xylene; ketones, such as acetone, acetophenone, methyl ethyl ketone or methyl butyl ketone.

It is also possible to use mixtures of the solvents and diluents mentioned for the process 2 according to the invention.

However, preferred diluents for carrying out the process 2 according to the invention are ethers, such as methyl tert-butyl ether or cyclic ethers, such as tetrahydrofuran and dioxane, amides, such as N,N-dimethylformamide, aromatic hydrocarbons, such as benzene or toluene; ketones, such as acetone, methyl ethyl ketone or methyl butyl ketone.

Suitable for use as basic reaction auxiliaries for carrying out the process 2 according to the invention are all suitable acid binders, such as amines, in particular tertiary amines, and also alkali metal and alkaline earth metal compounds.

Examples which may be mentioned are the hydroxides, hydrides, oxides and carbonates of lithium, sodium, potassium, magnesium, calcium and barium, furthermore other basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, chinoline, α-picoline, β-picoline, isochinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethyl-cyclohexylamine, 2,6-lutidine, 2,4-lutidine or triethyldiamine.

Preference is given to using hydrides of lithium or sodium.

The reaction time is generally from 10 minutes to 48 hours.

The reaction is carried out at temperatures between −10° C. and +200° C., preferably between +10° C. and 180° C., particularly preferably between 60° C. and 140° C. In principle, the reaction can be carried out under atmospheric pressure. The reaction is preferably carried out under atmospheric pressure or under pressures of up to 15 bar and, if appropriate, under an atmosphere of protective gas (nitrogen, helium or argon).

For carrying out the process 2 according to the invention, in general from 0.5 to 4.0 mol, preferably from 0.7 to 3.0 mol, particularly preferably from 1.0 to 2.0 mol of alkylating agent of the general formula (IV) are employed per mole of the compound of the formula (II).

After the reaction has gone to completion, the entire reaction mixture is concentrated. The products obtained after work-up can be purified in a customary manner by recrystallisation, distillation under reduced pressure or column chromatography (cf. also the Preparation Examples).

If, in the process 3 according to the invention for preparing the novel compounds of the formula (I), in a first reaction step, the compound of the formula (II) used is, for example, tetronic acid and the compound of the formula (V) is 2-fluoroethylamine hydrochloride, and, in a second reaction step, the resulting compound of the general formula (VI) is 4-[(2-fluoroethyl)amino)furan-2(5H)-one, which is N-alkylated with compounds of the formula (VII), for example 3-bromomethyl-5,6-dichloropyridine, the preparation process 3 can be represented by reaction scheme VII below:

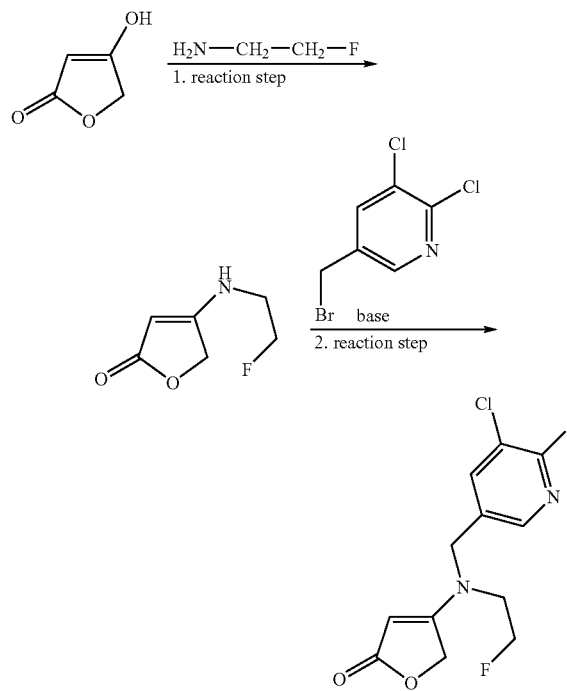

Scheme VII

The formula (II) provides a general definition of the compounds required as starting materials for carrying out the process 3 according to the invention and have already been described in more detail in connection with process 1, mentioned further above.

The formula (V) provides a general definition of the compounds further to be used as starting materials for carrying out the process 3 according to the invention.

In formula (V), $R^1$ has the meaning already mentioned in connection with the description of the compounds of the general formula (I) according to the invention.

The amino compounds of the formula (V) are defined in a general manner, and in many cases some of them are commercially available, or they can be obtained in a manner known per se by the Leuckart-Wallach reaction (for example 2-fluoroethylamine: U.S. Pat. No. 4,030,994 (1977); compounds of the general formula V in which $R^1$ represents alkyl, primary amines: cf., for example, Houben-Weyl, Methoden der Organischen Chemie, Vol. XI/1, 4. Ed. 1957, G. Thieme Verlag, Stuttgart, p. 648; M. L. Moore in "The Leuckart Reaction" in: Organic Reactions, vol. 5, 2. Ed. 1952, New York, John Wiley & Sons, Inc. London).

In general, it is advantageous to carry out the preparation process 3 according to the invention in the presence of diluents. Diluents are advantageously employed in such an amount that the reaction mixture remains readily stirrable during the entire process. Suitable diluents for carrying out the process 3 according to the invention are all inert organic solvents.

Preferred diluents for carrying out the process 3 according to the invention are aromatic hydrocarbons, such as benzene, toluene, chlorobenzene, bromobenzene, nitrobenzene or xylene, in particular benzene and toluene.

In the second reaction step, the compounds of the formula (VI) are N-alkylated with compounds of the formula (VII).

In general, it is advantageous to carry out the second reaction step of the preparation process 3 according to the invention in the presence of diluents and in the presence of basic reaction auxiliaries.

Diluents are advantageously employed in such an amount that the reaction mixture remains readily stirrable during the entire process. Suitable diluents for carrying out the process 3 according to the invention are all inert organic solvents.

Suitable diluents for the second reaction step are, for example, ethers, such as tetrahydrofuran or dioxane.

Suitable basic reaction auxiliaries for the second reaction step are strong bases, such as, for example, sodium hydride.

The reaction time is generally from 10 minutes to 48 hours.

The reaction is carried out at temperatures between −10° C. and +200° C., preferably between +10° C. and 180° C., particularly preferably between 60° C. and 140° C. The reaction is preferably carried out under reaction conditions which allow water to be separated off or to be removed, for example with the aid of a water separator.

After the reaction has gone to completion, the entire reaction mixture is concentrated. The products obtained after work-up can be purified in a customary manner by recrystallisation, distillation under reduced pressure or column chromatography (cf. also the Preparation Examples).

If appropriate, the compounds of the formula (I) can be present in different polymorphic forms or as a mixture of different polymorphic forms. Both the pure polymorphs and the polymorph mixtures are provided by the invention and can be used according to the invention.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogo-derma* spp., *Tychius* spp., *Xylotrechus* spp., *Zabrus* spp.

From the order of the Collembola, for example, *Onychiurus armatus.*

From the order of the *Dermaptera*, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the *Homoptera*, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the *Hymenoptera*, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the *Isoptera*, for example, *Reticulitermes* spp., *Odontotermes* spp.

From the order of the *Lepidoptera*, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia* kuehniella, *Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the *Siphonaptera*, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:
Inhibitors of nucleic acid synthesis
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
Inhibitors of mitosis and cell division
benomyl, carbendazim, diethofencarb, fuberidazole, pencycuron, thiabendazole, thiophanatmethyl, zoxamide
Inhibitors of respiratory chain complex I
diflumetorim
Inhibitors of respiratory chain complex II
boscalid, carboxin, fenfuram, flutolanil, furametpyr, mepronil, oxycarboxin, penthiopyrad, thifluzamide
Inhibitors of respiratory chain complex III
azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
dinocap, fluazinam
Inhibitors of ATP production
fentin acetate, fentin chloride, fentin hydroxide, silthiofam
Inhibitors of amino acid biosynthesis and protein biosynthesis
andoprim, blasticidin-S, cyprodinil, kasugamycin, kasugamycin hydrochloride hydrate, mepanipyrim, pyrimethanil
Inhibitors of signal transduction
fenpiclonil, fludioxonil, quinoxyfen
Inhibitors of lipid and membrane synthesis
chlozolinate, iprodione, procymidone, vinclozolin
ampropylfos, potassium-ampropylfos, edifenphos, iprobenfos (IBP), isoprothiolane, pyrazophos
tolclofos-methyl, biphenyl
iodocarb, propamocarb, propamocarb hydrochloride
Inhibitors of ergosterol biosynthesis
fenhexamid,
azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
aldimorph, dodemorph, dodemorph acetate, fenpropimorph, tridemorph, fenpropidin, spiroxamine,
naftifine, pyributicarb, terbinafine
Inhibitors of cell wall synthesis
benthiavalicarb, bialaphos, dimethomorph, flumorph, iprovalicarb, polyoxins, polyoxorim, validamycin A
Inhibitors of melanin biosynthesis
capropamid, diclocymet, fenoxanil, phthalid, pyroquilon, tricyclazole
Resistance inductors
acibenzolar-S-methyl, probenazole, tiadinil
Multisite
captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Unknown mechanism
amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxy-quinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridine-carboxamide, 3-[5-(4-chlorophenyl)-2,3-dimethylisoxazolidin-3-yl] pyridine, cis-1-(4-chloro-phenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy-phenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2 S)—N-[2-4-[[3-(4-chlorophenyl)-2-propynyl]oxy]-3-methoxyphenyl]ethyl]-3-methyl-2-[(methylsulphon-yl)amino]butanamide, 5-chloro-7-(4-methylpiperidin-1-yl)-6-(2,4,6-trifluorophenyl)[1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloro-nicotinamide, 2-butoxy-6-iodo-3-propylbenzopyranon-4-one, N-{(Z)-[(cyclopropylmethoxy)-imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3 (1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methyl-acetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine esterase (AChE) inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion
Sodium channel modulators/voltage-dependent sodium channel blockers
pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cyclopothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, trans-fluthrin, ZXI 8901, pyrethrins (pyrethrum)

DDT
oxadiazines,
for example indoxacarb
semicarbazones,
for example metaflumizone (BAS3201)

Acetylcholine Receptor Agonists/Antagonists
chloronicotinyls,
for example acetamiprid, clothianidin, dinotefuran, imidacloprid, nitenpyram, nithiazine, thiacloprid, imidaclothiz, AKD-1022, thiamethoxam
nicotine, bensultap, cartap Acetylcholine receptor modulators
spinosyns,
for example spinosad, spinetoram (XDE-175)

GABA-Controlled Chloride Channel Antagonists
organochlorines,
for example camphechlor, chlordane, endosulphan, gamma-HCH, HCH, heptachlor, lindane, methoxychlor
fiprols,
for example acetoprole, ethiprole, fipronil, pyrafluprole, pyriprole, vaniliprole Chloride Channel Activators
mectins,
for example abamectin, emamectin, emamectin-benzoate, ivermectin, lepimectin, milbemycin Juvenile Hormone Mimetics,
for example diofenolan, epofenonane, fenoxycarb, hydroprene, kinoprene, methoprene, pyriproxifen, triprene Ecdysone Agonists/Disruptors
diacylhydrazines,
for example chromafenozide, halofenozide, methoxyfenozide, tebufenozide Chitin Biosynthesis Inhibitors
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine Oxidative Phosphorylation Inhibitors, ATP Disruptors
diafenthiuron
organotin compounds,
for example azocyclotin, cyhexatin, fenbutatin-oxide Oxidative Phosphorylation Decouplers Acting by Interrupting the H-Proton Gradient
pyrroles,
for example chlorfenapyr
dinitrophenols, for example binapacyrl, dinobuton, dinocap, DNOC
Site-I Electron Transport Inhibitors
METIs,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Lipid Synthesis Inhibitors
tetronic acids,
for example spirodiclofen, spiromesifen
tetramic acids,
for example spirotetramat
carboxamides,
for example flonicamid
octopaminergic agonists,
for example amitraz
Inhibitors of Magnesium-Stimulated ATPase,
propargite
nereistoxin analogues,
for example thiocyclam hydrogen oxalate, thiosultap-sodium
Ryanodin Receptor Agonists
benzoic acid dicarboxamides,
for example flubendiamid
anthranilamides,
for example rynaxypyr (3-bromo-N-{4-chloro-2-methyl-6-[(methylamino)carbonyl]phenyl}-1-(3-chloropyridin-2-yl)-1H-pyrazole-5-carboxamide)
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
fumigants,
for example aluminium phosphide, methyl bromide, sulphuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compound combinations is carried out directly or by allowing the compounds to act on the surroundings, habitat or storage space by the customary treatment methods, for example by immersion, spraying, evaporation, fogging, scattering, painting on and, in the case of propagation material, in particular in the case of seeds, also by applying one or more coats.

The mixtures according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resulting plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the insecticidal individual active compound, which exceeds the activity to be expected of the two active compounds when applied individually. Also advantageous is the synergistically increased fungicidal activity of the compositions according to the invention in comparison with the fungicidal individual active compound, which exceeds the activity to be expected of the active compound when applied individually. This makes possible an optimization of the amount of active compound employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus spp.*, *Hippobosca* spp., *Lipoptena* spp., *Melophagus* spp. From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Process 1

4-[[(6-Chloro-5-fluoropyridin-3-yl)methyl](2,2-difluoroethyl)amino]furan-2(5H)-one Example (1)

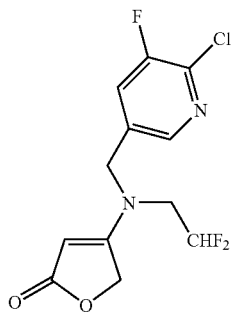

317 mg (1.41 mmol) of N-[(6-chloro-5-fluoropyridin-3-yl)methyl]-2,2-difluoroethylamine (III-1) are added to 173 mg (1.69 mmol) of tetronic acid in 400 μA of acetic acid, and the mixture is stirred at room temperature for 6 hours. The reaction mixture is concentrated under reduced pressure, and the residue is then partitioned between dichloromethane and water. The aqueous phase is extracted two more times with dichloromethane. The combined organic phases are washed with 1 N aqueous sodium hydroxide solution and concentrated under reduced pressure. Purification of the residue by column chromatography on silica gel (silica gel 60-Merck, particle size: 0.04 to 0.063 mm) using the mobile phase mixture ethyl acetate:cyclohexane (3:1) gives 316 mg (64% of theory) of 4-[[(6-chloro-5-fluoropyridin-3-yl)methyl](2,2-difluoroethyl)amino]furan-2(5H)-one.

$^1$H-NMR (CD$_3$CN): δ[ppm]=3.60 (td, 2H), 4.54 (s, 2H), 4.75 (s, 1H), 4.80 (s, 2H), 6.04 (tt, 1H), 7.54 (d, 1H), 8.15 (s, 1H).

Process 3

4-[[(5,6-Dichloropyridin-3-yl)methyl](2-fluoroethyl)amino]furan-2(5H)-one

Example (2)

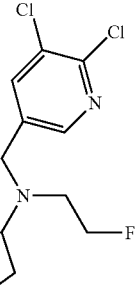

217 mg (1.49 mmol) of 4-[(2-fluoroethyl)amino]furan-2(5H)-one (VI-1) and 90 mg (2.24 mmol) of a 60% strength dispersion of sodium hydride in mineral oil in 100 ml of tetrahydrofuran are heated under reflux for 2 hours. After cooling to room temperature, 360 mg (1.49 mmol) of 3-(bromomethyl)-5,6-dichloropyridine are added, and the mixture is heated under reflux for a further 3 hours. After cooling to room temperature and addition of methanol, the reaction mixture is concentrated under reduced pressure. The residue is taken up in ethyl acetate, washed successively twice with 1 N aqueous hydrochloric acid, twice with 1 N aqueous sodium hydroxide solution and saturated sodium chloride solution and dried over sodium sulphate. After concentration of the organic phase under reduced pressure and purification of the residue by column chromatography on silica gel (silica gel 60-Merck, particle size: 0.04 to 0.063 mm) using the mobile phase mixture ethyl acetate:cyclohexane (5:1), 260 mg (56% of theory) of 4-[[(5,6-dichloropyridin-3-yl)methyl](2-fluoroethyl)amino]furan-2(5H)-one are obtained.

$^1$H-NMR (CD$_3$CN): δ[ppm]=3.50 (dt, 2H), 4.49 (s, 2H), 4.55 (dt, 2H), 4.64 (s, 1H), 4.80 (s, 2H), 7.80 (s, 1H), 8.22 (s, 1H).

The compounds (3) to (7) of the formula (I) listed in Table 1 below were also prepared analogous to this procedure.

TABLE 1

Compounds of the formula (I)

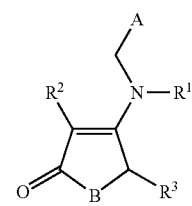

in which A =

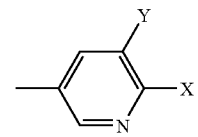

| Ex. No. | B | R$^1$ | R$^2$ | R$^3$ | X | Y | Physical data: $^1$H—NMR, δ [ppm] |
|---|---|---|---|---|---|---|---|
| 3 | O | CH(CH$_3$)CH$_2$F (2-fluoropropyl group shown in structure) | H | H | Cl | Cl | CD$_3$CN, δ = 3.59 (td, 2H), 4.52 (s, 2H), 4.75 (s, 1H), 4.80 (s, 2H), 6.04 (tt, 1H), 7.80 (s, 1H), 8.22 (s, 1H) |

TABLE 1-continued

Compounds of the formula (I)

in which A =

| Ex. No. | B | R¹ | R² | R³ | X | Y | Physical data: ¹H—NMR, δ [ppm] |
|---|---|---|---|---|---|---|---|
| 4 | O |  F | H | H | Cl | CH₃ | $CD_3CN$, δ = 2.35 (s, 3H), 3.57 (td, 2H), 4.48 (s, 2H), 4.75 (s, 1H), 4.80 (s, 2H), 6.02 (tt, 1H), 7.54 (s, 1H), 8.11 (s, 1H) |
| 5 | O |  F | H | H | Cl | Br | $CD_3CN$, δ = 3.60 (td, 2H), 4.50 (s, 2H), 4.75 (s, 1H), 4.80 (s, 2H), 6.04 (tt, 1H), 7.95 (s, 1H), 8.25 (s, 1H) |
| 6 | O | (same as above) F | H | H | Br | Cl | $CD_3CN$, δ = 3.60 (td, 2H), 4.50 (s, 2H), 4.75 (s, 1H), 4.80 (s, 2H), 6.04 (tt, 1H), 7.75 (s, 1H), 8.20 (s, 1H) |
| 7 | O | (same as above) F | H | H | Br | F | $CD_3CN$, δ = 3.61 (td, 2H), 4.53 (s, 2H), 4.75 (s, 1H), 4.80 (s, 2H), 6.04 (tt, 1H), 7.47 (d, 1H), 8.14 (s, 1H) |

Preparation of the Starting Materials

Compounds of the formula (HN(R¹)—CH₂-A) (III)

III-1

N-[(6-Chloro-5-fluoropyridin-3-yl)methyl]-2,2-difluoroethylamine

At 45° C., 520 mg (2.89 mmol) of 6-chloro-3-chloromethyl-5-fluoropyridine (VII-3), 1.05 ml (14.44 mmol) of 2,2-difluoroethylamine and 400 μL (2.89 mmol) of triethylamine are stirred in 50 ml of acetonitrile for about 48 hours. After about 16 and 32 hours, in each case another 0.42 ml (5.78 mmol) of 2,2-difluoroethylamine are added. After concentration of the reaction mixture under reduced pressure, the residue is taken up in 1 N aqueous hydrochloric acid and the mixture is washed with ethyl acetate. The aqueous phase is made alkaline using 2.5 N aqueous sodium hydroxide solution and extracted repeatedly with ethyl acetate. The combined organic phase is dried over sodium sulphate and concentrated under reduced pressure, giving 370 mg (57% of theory) of N-[(6-chloro-5-fluoropyridin-3-yl)methyl]-2,2-difluoroethylamine.

¹H-NMR ($CD_3CN$): δ [ppm]=2.95 (td, 2H), 3.87 (s, 2H), 5.87 (ft, 1H), 7.62 (d, 1H), 8.17 (s, 1H).

Compounds of the formula (VI)

VI-1

4-[(2-Fluoroethyl)amino]furan-2(5H)-one

On a water separator, 550 mg (4.97 mmol) of 2-fluoroethylamine hydrochloride, 547 mg (5.47 mmol) of tetronic acid, 408 mg (4.97 mmol) of sodium acetate and 9 mg (0.05 mmol) of 4-toluenesulphonic acid in 50 ml of toluene are heated for 5 hours under reflux. The reaction mixture is concentrated under reduced pressure, the residue is taken up in ethyl acetate and the mixture is washed with 1 N aqueous sodium hydroxide solution. The aqueous phase is extracted repeatedly with ethyl acetate and the combined organic phase is dried over sodium sulphate. The organic phase is concentrated under reduced pressure and the residue is purified by recrystallisation from ethyl acetate/cyclohexane, giving 300 mg (42% of theory) of 4-[(2-fluoroethyl)amino]furan-2(5H)-one.

¹H-NMR ($CD_3CN$, δ, ppm)=3.40 (dq, 2H), 4.52 (dt, 2H), 4.61 (s, 1H), 4.62 (s, 2H), 5.80 (br. s, 1H).

Compound (VI-2) was also prepared analogously to this procedure:

VI-2

4-[(2,2-Difluoroethyl)amino]furan-2(5H)-one $^1$H-NMR (CD$_3$CN, δ, ppm)=3.50 (tm, 2H), 4.65 (s, 2H), 4.71 (s, 1H), 5.78 (br. s, 1H), 5.98 (tt, 1H).

Compounds of the formula (E-CH$_2$-A) (VII)

VII-1

(5,6-Dichloropyridin-3-yl)methanol (E=OH, A=5,6-dichloropyrid-3-yl) (cf. R. Graf et al. J. Prakt. Chem. 1932, 134 177-87)

At 0° C., 859 ml (859 mmol) of a 1 M solution of borane-tetrahydrofuran complex in tetrahydrofuran are added dropwise to 110 g (573 mmol) of 5,6-dichloronicotinic acid in 250 ml of tetrahydrofuran. The mixture is warmed to room temperature and stirred at this temperature for 3 hours. After cooling to 0° C., the reaction mixture is made alkaline with saturated aqueous potassium carbonate solution, most of the tetrahydrofuran is removed using a rotary evaporator and the residue is extracted repeatedly with ethyl acetate. The combined organic phases are washed with water and saturated aqueous sodium chloride solution and dried over sodium sulphate. Concentration of the organic phase under reduced pressure and purification of the residue by column chromatography on silica gel (silica gel 60-Merck, particle size: 0.04 to 0.063 mm) using the mobile phase mixture ethyl acetate:cyclohexane (1:2) gives 62 g (61% of theory) of (5,6-dichloropyridin-3-yl)methanol.

$^1$H-NMR (CD$_3$CN): δ [ppm]=3.31 (t, 1H), 4.60 (d, 2H), 7.85 (s, 1H), 8.26 (s, 1H)

Compound (VII-5) from Table 3 was also prepared analogously to the procedure for the compound (VII-1).

VII-2

3-Bromomethyl-5,6-dichloropyridine (E=Br, A=5,6-dichloropyrid-3-yl) (cf. WO 2000046196 A1)

At 0° C., 16.40 g (62.52 mmol) of triphenylphosphine and 11.66 g (65.50 mmol) of N-bromosuccinimide are added to a solution of 10.60 g (59.55 mmol) of (5,6-dichloropyridin-3-yl)methanol (VII-1) in 100 ml of dichloromethane. After 2 hours, the reaction mixture is substantially concentrated and the residue is purified by column chromatography on silica gel (silica gel 60-Merck, particle size: 0.04 to 0.063 mm) using the mobile phase mixture ethyl acetate:cyclohexane (1:5). This gives 12.4 g (86% of theory) of 3-bromomethyl-5,6-dichloropyridine.

$^1$H-NMR (CD$_3$CN): δ [ppm]=4.53 (s, 2H), 7.97 (s, 1H), 8.35 (s, 1H)

The compounds (VII-6) to (VII-8) from Table 3 were also prepared analogously to the procedure for the compound (VII-2).

VII-3

6-Chloro-3-chloromethyl-5-fluoropyridine (E=Cl, A=6-chloro-5-fluoropyrid-3-yl)

1.00 g (6.87 mmol) of 6-chloro-5-fluoro-3-methylpyridine (cf. F. L. Setliff, Organic Preparations and Procedures International 1971, 3, 217-222), 1.01 g (7.56 mmol) of N-chlorosuccinimide and 0.11 g (0.69 mmol) of 2,2'-azobis(2-methylpropanenitrile) in 100 ml of chlorobenzene are boiled under reflux for 2 days. After about 16 and 32 hours, in each case a further 1.01 g (7.56 mmol) of N-chlorosuccinimide and 0.11 g (0.69 mmol) of 2,2'-azobis(2-methylpropanenitrile) are added. The reaction mixture is washed with saturated aqueous sodium sulphite solution and sodium bicarbonate solution and then dried over sodium sulphate and concentrated under reduced pressure. Column chromatography of the residue on silica gel (silica gel 60-Merck, particle size: 0.04 to 0.063 mm) using the mobile phase mixture ethyl acetate:cyclohexane (1:20) gives 0.65 g (53% of theory) 6-chloro-3-chloromethyl-5-fluoropyridine.

$^1$H-NMR (CD$_3$CN): δ[ppm]=4.68 (s, 2H), 7.69 (d, 1H), 8.27 (s, 1H)

VII-4

6-Bromo-3-bromomethyl-5-fluoropyridine (E=Br, A=6-bromo-5-fluoropyrid-3-yl)

10.00 g (52.63 mmol) of 6-bromo-5-fluoro-3-methylpyridin (cf. F. L. Setliff, Organic Preparations and Procedures International 1971, 3, 217-222), 12.18 g (68.42 mmol) of N-bromosuccinimide and 0.86 g (5.26 mmol) of 2,2'-azobis (2-methylpropanenitrile) in 1 of chlorobenzene are boiled under reflux for 6 hours. The reaction mixture is washed with saturated aqueous sodium sulphite solution and sodium bicarbonate solution and then dried over sodium sulphate and concentrated under reduced pressure. Column chromatography of the residue on silica gel (silica gel 60-Merck, particle size: 0.04 to 0.063 mm) using the mobile phase mixture ethyl acetate:cyclohexane (1:20) gives 6.0 g (42% of theory) of 6-bromo-3-chloromethyl-5-fluoropyridine.

$^1$H-NMR (CD$_3$CN): δ [ppm]=4.55 (s, 2H), 7.65 (d, 1H), 8.27 (s, 1H)

Further compounds (VII-5) to (VII-8) of the formula (VII) are listed in Table 3 below.

TABLE 3

(VII) E—CH$_2$—A

| Ex. No. | E | A | Physical Data[a)] |
|---|---|---|---|
| VII-5 | OH | 3-chloro-5-methyl-2-bromopyridin-... | 3.30 (t, 1H), 4.59 (d, 2H), 7.83 (s, 1H), 8.26 (s, 1H) |

TABLE 3-continued (VII)
E—CH$_2$—A

| Ex. No. | E | A | Physical Data[a] |
|---|---|---|---|
| VII-6 | Br | (structure: 3-methyl-2-chloro-5-methylpyridine with CH$_2$ at 4-position) | 2.37 (s, 3H), 4.52 (s, 2H), 7.70 (s, 1H), 8.24 (s, 1H) |
| VII-7 | Br | (structure: 3-bromo-2-chloro-5-methylpyridine with CH$_2$ at 4-position) | 4.52 (s, 2H), 8.10 (s, 1H), 8.38 (s, 1H) |
| VII-8 | Br | (structure: 3-chloro-2-bromo-5-methylpyridine with CH$_2$ at 4-position) | 4.52 (d, 2H), 7.92 (s, 1H), 8.35 (s, 1H) |

[a] $^1$H—NMR (CD$_3$CN), δ [ppm]

BIOLOGICAL EXAMPLES

Example No. 1

Myzus Test (MYZUPE Spray Treatment)

| | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with a preparation of active compound of the desired concentration.

After the desired period of time, the effect in % is determined 100% means that all aphids have been killed; 0% means that none of the aphids have been killed.

In this test, for example, the following compounds of the Preparation Examples show good activity: see table

| Example | Active compound concentration in g/ha | Kill rate in % after 5 days |
|---|---|---|
| Example 1 | 500 | 100 |
| Example 2 | 500 | 100 |
| Example 3 | 500 | 100 |
| Example 4 | 500 | 100 |
| Example 5 | 500 | 100 |
| Example 6 | 500 | 100 |
| Example 7 | 500 | 100 |

Example No. 2

*Nilanarvata lugens* Test (NILALU Hydrononic Treatment)

| | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

The preparation of active compound is pipetted into water. The stated concentration refers to the amount of active compound per volume unit of water (mg/l=ppm). The water is then infected with the brown planthopper (*Nilaparvata lugens*).

After the desired period of time, the effect in % is determined. 100% means that all planthoppers have been killed; 0% means that none of the planthoppers have been killed.

In this test, for example, the following compounds of the Preparation Examples show good activity: see table

| Example | Active compound concentration in g/ha | Kill rate in % after 7 days |
|---|---|---|
| Example 2 | 100 | 80 |
| Example 3 | 100 | 100 |

Example No. 3

*Bemisia tabaci* (BEMITA Spray Treatment)

| | |
|---|---|
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Discs of cotton leaves (*Gossypium hirsutum*) which are infested by larvae of the whitefly (*Bemisia tabaci*) are sprayed with a preparation of active compound of the desired concentration.

After the desired period of time, the effect in % is determined 100% means that all whiteflies have been killed; 0% means that none of the whiteflies have been killed.

In this test, for example, the following compounds of the Preparation Examples show good activity: see table

| Example | Active compound concentration in g/ha | Kill rate in % after 7 days |
|---|---|---|
| Example 1 | 500 | 100 |

Example No. 4

*Meloidogyne* Test (MELGIN Spray Treatment)

| | |
|---|---|
| Solvent: | 80 parts by weight of acetone |

To produce a suitable preparation of active compound, 1 part by weight of active compound is mixed with the stated amounts of solvent and emulsifier, and the concentrate is diluted with water to the desired concentration.

Containers are filled with sand, active compound solution, *Meloidogyne incognita* egg/larvae suspension and lettuce seeds. The lettuce seeds germinate and the plants develop. On the roots, galls are formed.

After the desired period of time, the nematicidal activity is determined by the formation of galls in %. 100% means that no galls were found; 0% means that the number of galls on the treated plants corresponds to that of the untreated controls.

In this test, for example, the following compounds of the Preparation Examples show good activity: see table

| Example | Active compound concentration in ppm | Kill rate in % after 14 days |
|---|---|---|
| Example 2 | 20 | 100 |

Example No. 5

*Myzus persicae* Test, Hydroponic Treatment (MYZUPE Sys.)

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration refers to the amount of active compound per volume unit of water (mg/l=ppm). The treated water is filled into containers housing a pea plant (*Pisum sativum*) which is then infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 6 days |
|---|---|---|
| Example 2 | 20 | 100 |

Example No. 6

*Aphis gossypii* Test (APHIGO)

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined 100% means that all aphids have been killed; 0% means that none of the aphids have been killed.

In this test, for example, the following compounds of the Preparation Examples show good activity: see table

| Example | Active compound concentration in ppm | Kill rate in % after 6 days |
|---|---|---|
| Example 2 | 100 | 95 |

Example No. 7

*Myzus persicae* Test; (MYZUPE G)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cabbage plants (*Brassica oleracea*) which are heavily infested by the green peach aphid (*Myzus persicae*) are watered with a preparation of active compound of the desired concentration.

After the desired period of time, the kill in % is determined 100% means that all aphids have been killed; 0% means that none of the aphids have been killed.

In this test, for example, the following compounds of the Preparation Examples show good activity: see table

| Example | Active compound concentration in ppm | Kill rate in % after 10 days |
|---|---|---|
| Example 2 | 4 | 98 |

Example No. 8

*Aphis gossypii* Test; (APHIGO G)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cotton plants (*Gossypium hirsutum*) which are heavily infested by the cotton aphid (*Aphis gossypii*) are watered with a preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 10 days |
|---|---|---|
| Example 2 | 4 | 100 |

Example No. 9

*Myzus persicae* Test (Soil Application)

| Solvent: | 4 parts by weight of acetone |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is mixed with soil. The stated concentration refers to the amount of active compound per volume unit of soil (mg/l=ppm). The treated soil is filled into pots and planted with a bell pepper plant (*Capsicum annuum*). After one week, the plant is infected with the green peach aphid (*Myzus persicae*).

After the desired period of time, the kill in % is determined 100% means that all aphids have been killed; 0% means that none of the aphids have been killed.

In this test, for example, the following compounds of the Preparation Examples show good activity: see table

| Example | Active compound concentration in ppm | Kill rate in % after 35 days |
|---|---|---|
| Example 4 | 0.25 | 90 |

Example No. 10

*Ctenocephalides felis*; Oral (CTECFE)

| Solvent: | dimethyl sulphoxide |
|---|---|

To produce a suitable preparation of active compound, 1 part by weight of active compound is mixed with the stated amount of solvent. Part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. The blood is warmed to 37° C., but the flea chamber is at room temperature.

After the desired period of time, the kill in % is determined 100% means that all fleas have been killed; 0% means that none of the fleas have been killed.

In this test, for example, the following compounds of the Preparation Examples show good activity: see table

| Example | Active compound concentration in ppm | Kill rate in % after 2 days |
|---|---|---|
| Example 1 | 100 | 80 |
| Example 3 | 100 | 80 |
| Example 4 | 100 | 80 |
| Example 6 | 100 | 80 |

Example No. 11

*Lucilia cuprina* Test (LUCICU)

| Solvent: | dimethyl sulphoxide |
|---|---|

To produce a suitable preparation of active compound, 1 part by weight of active compound is mixed with the stated amounts of solvent, and the concentrate is diluted with water to the desired concentration.

Containers containing horse meat treated with the preparation of active compound of the desired concentration are populated with *Lucilia cuprina* larvae.

After the desired period of time, the kill in % is determined 100% means that all larvae have been killed; 0% means that none of the larvae have been killed.

In this test, for example, the following compounds of the Preparation Examples show good activity: see table

| Example | Active compound concentration in ppm | Kill rate in % after 2 days |
|---|---|---|
| Example 1 | 100 | 100 |
| Example 7 | 100 | 100 |

Example No. 12

*Boophilus microplus* Test (BOOPMI Injection)

| Solvent: | dimethyl sulphoxide |
|---|---|

To produce a suitable preparation of active compound, 1 part by weight of active compound is mixed with the stated amount of solvent, and the concentrate is diluted with solvent to the desired concentration.

The solution of active compound is injected into the abdomen (*Boophilus microplus*), and the animals are transferred into dishes and kept in a temperature-controlled room.

After the desired period of time, the effect in % is determined. 100% means that no tick has laid any fertile eggs.

In this test, for example, the following compounds of the Preparation Examples show good activity: see table

| Example | Active compound concentration in µg/animal | Kill rate in % after 7 days |
|---|---|---|
| Example 2 | 20 | 100 |

The invention claimed is:

1. A compound of formula (I)

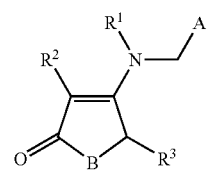

(I)

in which

A represents one of the radicals pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which are optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or A represents a radical

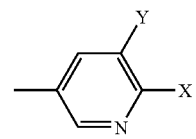

in which

X represents halogen, alkyl or haloalkyl,

Y represents halogen, alkyl, haloalkyl, haloalkoxy, azido or cyano,

B represents oxygen, sulphur or methylene, $R^1$ represents haloalkyl, haloalkenyl, halocycloalkyl or halocycloalkylalkyl, $R^2$ represents hydrogen or halogen and $R^3$ represents hydrogen or alkyl.

2. A compound of formula (I)

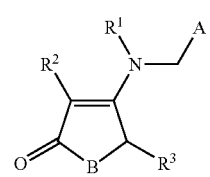

(I)

in which

A represents a pyrimidin-5-yl radical which is substituted in the 2-position by halogen or halo-$C_1$-$C_4$-alkyl, or A represents a radical

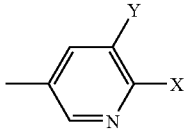

in which

X represents halogen, $C_1$-$C_1$-alkyl or halo-$C_1$-$C_4$-alkyl,

Y represents halogen, $C_1$-$C_4$-alkyl, halo-$C_1$-$C_4$-alkyl, halo-$C_1$-$C_4$-alkoxy, azido or cyano, B represents oxygen, sulphur or methylene, $R^1$ represents halo-$C_1$-$C_3$-alkyl, halo-$C_2$-$C_3$-alkenyl, halocyclopropyl, $R^2$ represents hydrogen or halogen and $R^3$ represents hydrogen or alkyl.

3. A composition, comprising at least one compound of formula (I) according to claim 1 with an extender and/or surfactant.

4. A method for controlling a pest, comprising allowing a compound of formula (I) according to claim 1 to act on the pest and/or a habitat thereof.

5. A composition according to claim 3 for controlling pests.

6. A composition comprising at least one compound of formula (I) according to claim 2, with an extender and/or a surfactant.

7. A method for controlling a pest comprising allowing a compound of formula (I) according to claim 2 to act on the pest and/or a habitat thereof.

8. A method for controlling a pest comprising allowing a composition according to claim 3 to act on the pest and/or a habitat thereof.

9. A composition according to claim 6 for controlling pests.

10. A compound according to claim 1, wherein A represents a radical

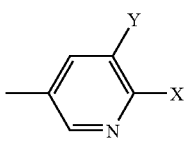

in which

X represents halogen, alkyl or haloalkyl, and

Y represents halogen, alkyl, haloalkyl, haloalkoxy, azido or cyano.

11. A compound according to claim 1, wherein A represents one of the radicals pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which are optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine).

12. A method for the manufacture of a compound of formula (I)

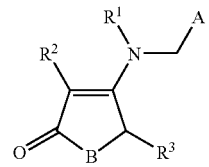

in which

A represents a radical

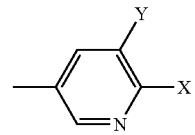

in which

X represents halogen, alkyl or haloalkyl,

Y represents halogen, alkyl, haloalkyl, haloalkoxy, azido or cyano,

B represents oxygen, sulphur or methylene, $R^1$ represents haloalkyl, haloalkenyl, halocycloalkyl or halocycloalkylalkyl, $R^2$ represents hydrogen or halogen and $R^3$ represents hydrogen or alkyl, which method comprises reacting a compound of formula (II)

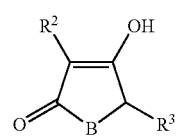

in which B, $R^2$, and $R^3$ are defined as above with a compound of formula (III)

$HN(R^1)$-$CH_2$-A    (III)

in which A and $R^1$ are as defined above, in the presence of an acidic auxiliary selected from p-toluenesulphonic acid or acetic acid and, optionally in the presence of a diluent.

13. A method according to claim 12, wherein the diluent is present and selected from the group consisting of benzene, toluene, chlorobenzene, bromobenzene, nitrobenzene, and xylene.

14. A method according to claim 13, wherein the reaction is carried out at temperatures between 20° C. and 140° C.

15. A method according to claim 12, wherein the compound of formula (II) is tetronic acid and the compound of formula (III) is N-[(6-chloro-5-fluoropyridin-3-yl) methyl]-2,2-difluoroethane-1-amine.

16. A compound of formula (III)

$HN(R^1)$-$CH_2$-A    (III)

in which
A represents a radical
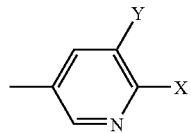
in which
X represents halogen, alkyl or haloalkyl,
Y represents halogen, alkyl, haloalkyl, haloalkoxy, azido or cyano, and
$R^1$ represents haloalkyl, haloalkenyl, halocycloalkyl or halocycloalkylalkyl.
17. The compound according to claim 16, wherein the compound of formula (III) is N-[(6-chloro-5-fluoropyridin-3-yl)methyl]-2,2-difuoroethane-1-amine.
* * * * *